(12) United States Patent
Tsuchiya et al.

(10) Patent No.: US 10,261,004 B2
(45) Date of Patent: Apr. 16, 2019

(54) DETERMINING DEVICE AND DETERMINING METHOD

(71) Applicant: CHEMICAL GROUTING CO., LTD., Tokyo (JP)

(72) Inventors: Tsutomu Tsuchiya, Tokyo (JP); Masanori Kumekawa, Tokyo (JP); Hiroyuki Abe, Tokyo (JP)

(73) Assignee: CHEMICAL GROUTING CO., LTD., Tokyo (JP)

( * ) Notice: Subject to any disclaimer, the term of this patent is extended or adjusted under 35 U.S.C. 154(b) by 112 days.

(21) Appl. No.: 15/535,943

(22) PCT Filed: Apr. 22, 2015

(86) PCT No.: PCT/JP2015/062199
§ 371 (c)(1),
(2) Date: Jun. 14, 2017

(87) PCT Pub. No.: WO2016/103750
PCT Pub. Date: Jun. 30, 2016

(65) Prior Publication Data
US 2017/0343456 A1    Nov. 30, 2017

(30) Foreign Application Priority Data

Dec. 24, 2014    (JP) ................................ 2014-259838

(51) Int. Cl.
*E02D 3/12* (2006.01)
*B05B 15/00* (2018.01)
(Continued)

(52) U.S. Cl.
CPC ............... *G01N 7/14* (2013.01); *B05B 15/00* (2013.01); *E02D 3/12* (2013.01); *G01M 17/00* (2013.01); *G01M 99/008* (2013.01)

(58) Field of Classification Search
CPC .......... E02D 3/12; B05B 15/00; G01M 13/00; G01M 99/00; G01M 99/008; G01N 7/14
See application file for complete search history.

(56) References Cited

FOREIGN PATENT DOCUMENTS

| CN | 102141467 A | * | 8/2011 | ............ G01M 13/00 |
| CN | 103148981 A | | 6/2013 | |

(Continued)

OTHER PUBLICATIONS

Extended European Search Report for corresponding European patent application No. 15872319.7, dated Jun. 13, 2018 (7 Sheets).

(Continued)

*Primary Examiner* — Nguyen Q. Ha
(74) *Attorney, Agent, or Firm* — Kratz, Quintos & Hanson, LLP (57) ABSTRACT

The purpose of the present invention is to provide a determining device and a determining method to determine whether an inspected jet nozzle is defective by inspecting the jet nozzle for injecting a jet stream with long ground penetrating distance at a stage before installing in a construction site where a large diameter jet grouting method is used. To achieve this purpose, with this invention, in which a nozzle to be inspected is mounted onto an outlet port, a jet stream is ejected from a jet stream generating device, and measurement data measured by a pressure sensing unit when the jet stream impacts the pressure sensing unit is processed with a controlling device (for example, a computer), a nozzle to be inspected is determined to be a non-defective product if a first ratio is no less than a first prescribed value, a second ratio is no less than a second prescribed value, and a third ratio is no less than a third prescribed value.

2 Claims, 4 Drawing Sheets

(51) Int. Cl.
*G01M 13/00* (2006.01)
*G01M 99/00* (2011.01)
*G01N 7/14* (2006.01)
*G01M 17/00* (2006.01)

(56) References Cited

FOREIGN PATENT DOCUMENTS

| | | |
|---|---|---|
| DE | 102008007332 A1 | 8/2009 |
| DE | 102011008002 A1 | 7/2012 |
| JP | S63-88425 A | 4/1988 |
| JP | H7-174668 A | 7/1995 |
| JP | H08-80477 A | 3/1996 |
| JP | 2014-62366 A1 | 4/2014 |
| WO | 2013125463 A2 | 8/2013 |

OTHER PUBLICATIONS

International Search Report for International Application No. PCT/JP2015/062199 dated Jun. 23, 2015.

\* cited by examiner

DETERMINING DEVICE AND DETERMINING METHOD

TECHNICAL FIELD

The present invention relates to a technology inspecting a jet nozzle which is used in a large diameter jet grouting method and constructed to generate a jet stream (a jet) with a long ground penetrating distance.

BACKGROUND ART

As one of the means to improve soft ground, a large diameter jet grouting method for constructing a column-shaped improvement body having a large radial dimension in the ground is well-known.

In this large diameter jet grouting method, it is necessary to inject a jet stream with a long distance (a ground penetrating or cutting distance) to penetrate or cut into the ground which is to be subjected to construct a column-shaped improvement body having a large radial dimension. Therefore, the quality of a jet nozzle must be maintained equal or better than a certain level. When a poor-quality jet nozzle is used, a jet stream reachable distance, i.e., the ground penetrating distance is shortened.

In order to avoid a situation that the jet stream reachable distance is shortened, it is necessary to examine a jet stream ejected from a jet nozzle at a stage before actually injecting the jet stream in a construction site carrying out the large diameter jet grouting method, and to determine whether the jet nozzle is good or defective.

However, there is no technology to correctly determine whether a jet nozzle is good or defective at the stage before actually injecting a jet stream in a construction site.

In a prior art, for example, a jet stream is caused to impact pressure sensitive paper, a degree of discoloration of the pressure sensitive paper after impacting the jet stream is observed, and then, it is possible to determine whether a jet nozzle is good or defective (see Patent Literature 1).

However, since the pressure sensitive paper discolors when a prescribed pressure is applied thereto, it is not possible to identify a point of time at which the prescribed pressure (or a higher pressure which causes discoloration) was applied even though the pressure sensitive paper discolored. Further, since the point of time at which the predetermined pressure was applied cannot be identified, there is a problem that even a defective nozzle, by which a pressure of a jet stream cannot act always uniformly, is determined to be a non-defective product.

As another prior art, a technology to examine whether an injection hole in a cleaning device which ejects a cleaning liquid with a high pressure is clogged has been proposed (see Patent Literature 2).

However, the cleaning device according to the prior art (Patent Literature 2) cannot be applied to ground improvement construction works.

CITATION LIST

Patent Literatures

Patent Literature 1: Japanese Patent Application Non-examined Publication Gazette No. 2014-62366 (JPA2014-62366)
Patent Literature 2: Japanese Patent Application Non-examined Publication Gazette No. H08-80477 (JPAH08-80477)

SUMMARY OF INVENTION

Problem to be Solved by the Invention

In view of the problems of the above-mentioned prior arts, it is an object of the present invention to provide a determining device and a determining method to determine whether an inspected jet nozzle is a defective product by inspecting the jet nozzle constructed to eject a jet stream (a jet) with along ground penetrating distance at a stage before installing in a construction site where a large diameter jet grouting method is carried out.

Means for Solving Problem

A determining device according to the present invention is characterized by comprising:
a jet stream generating device (a pump 1) having an outlet port to/from which a nozzle (N) as an inspection target is attachable/detachable;
a pressure sensing unit (2) with which a jet stream (J) ejected from the jet stream generating device (1) collides; and
a controlling device (an information processing device: e.g., a computer 10) to which a measurement result signal from the pressure sensing unit (2) is transmitted,
the controlling device (10) having:
a function for calculating an average value of pressures which enable to penetrate (pressures which enable to penetrate or cut into construction ground for a necessary distance) merely in a pressure distribution sensed by the pressure sensing unit (2) in each frame, and for determining whether a first ratio is equal to or more than a first prescribed value (e.g., 70%), said first ratio is a ratio of frames, in each of which a pressure being equal to or more than a first threshold value (a numerical value with which penetration into the construction ground is enabled for a necessary distance) is sensed, to a total number of frames where pressures from the nozzle (N) as the inspection target have been detected;
a function for calculating an area of a region where the pressures being enable to penetrate are distributed, and for determining whether a second ratio is equal to or more than a second prescribed value (e.g., 90%), said second ratio is a ratio of frames, an area of each of which is greater than zero but is not greater than a second threshold value, to the total number of frames where the pressures from the nozzle (N) as the inspection target have been detected;
a function for determining coordinates of pressure center in each frame, and for determining whether a third ratio is equal to or more than a third prescribed value (e.g., 90%), said third ratio is a ratio of frames, in each of which the pressure center coordinates is located within a prescribed range (e.g., within a circular region having a center which is an average value of the pressure center coordinates and having a diameter which is triple a nozzle diameter), to the total number of frames where the pressures from the nozzle (N) as the inspection target have been detected; and
a function for determining the nozzle (N) as the inspection target to be a non-defective product in a case that the first ratio is equal to or more than the first prescribed value, the second ratio is equal to or more than the second prescribed value, and the third ratio is equal to or more than the third prescribed value, and for determining the nozzle as the inspection target to be a defective product in any other case.

Figure 2:
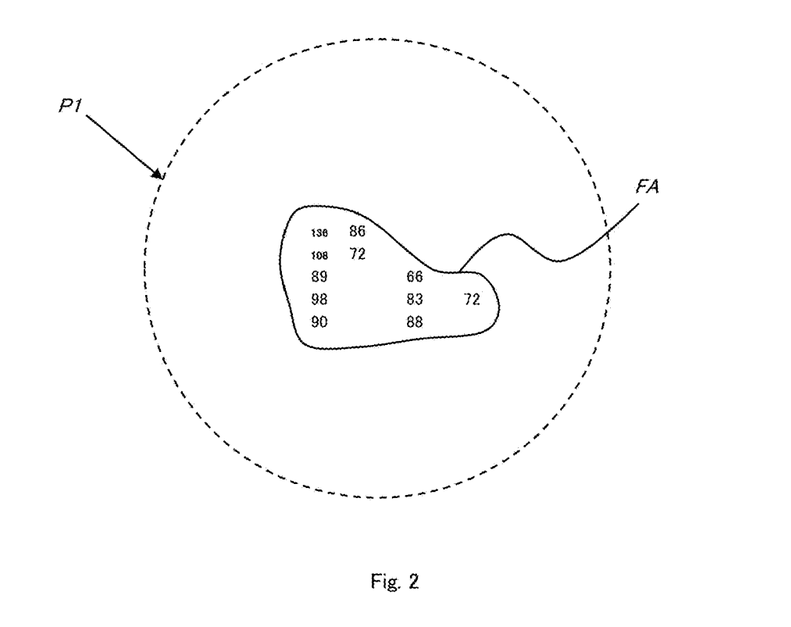
FIG. 2 is an explanatory drawing illustrating a frame (which is a measurement result per unit time, and only portions to which pressures enabling penetration into construction ground for a necessary distance acted show figures) in the embodiment.

Here, the word "frame" means a measurement result per unit time (see FIG. 2). Furthermore, said phrase "within a prescribed range (e.g., within a circular region having a center which is an average value of the pressure center coordinates and having a diameter which is triple a nozzle diameter)" is a circle shown in FIG. 3, center thereof is an average position of, e.g., 1000 plots, and the plots are the pressure center coordinates.

According to the determining method of the present invention, in which a nozzle (N) as an inspection target is mounted onto an outlet port, a jet stream (J) is ejected from a jet stream generating device (a pump device 1), and measurement results being measured by a pressure sensing unit (2) when the jet stream (J) impacts the pressure sensing unit (2) are processed by a controlling device (an information processing device: e.g., a computer 10), it is characterized by comprising:

a first determination step for calculating an average value of pressures which enable to penetrate (pressures which enable to penetrate or cut into construction ground for a necessary distance) merely in a pressure distribution sensed by the pressure sensing unit (2) in each of frame, and for determining whether a first ratio is equal to or more than a first prescribed value (e.g., 70%), said first ratio is a ratio of frames, in each of which a pressure being equal to or more than a first threshold value (a numerical value with which penetration into the construction ground is enabled for a necessary distance) is sensed, to a total number of frames where pressures from the nozzle (N) as the inspection target have been detected;

a second determination step for calculating an area of a region where the pressures being enable to penetrate are distributed, and for determining whether a second ratio is equal to or more than a second prescribed value (e.g., 90%), said second ratio is a ratio of frames, an area of each of which is greater than zero but is not greater than a second threshold value, to the total number of frames where the pressures from the nozzle (N) as the inspection target have been detected;

a third determination step for determining coordinates of pressure center in each frame, and for determining whether a third ratio is equal to or more than a third prescribed value (e.g., 90%), said third ratio is a ratio of frames, in each of which the coordinates of the pressure center is located within a prescribed range (e.g., within a circular region having a center which is an average value of the pressure center coordinates and having a diameter which is triple a nozzle diameter), to the total number of frame where the pressures from the nozzle (N) as the inspection target have been detected; and a step for determining the nozzle (N) as the inspection target to be a non-defective product in a case that the first ratio is equal to or more than the first prescribed value, the second ratio is equal to or more than the second prescribed value, and the third ratio is equal to or more than the third prescribed value, and for determining the nozzle (N) as the inspection target to be a defective product in any other case.

Here, the first threshold value, the second threshold value, the prescribed range, and the first to third prescribed values are determined on a case-by-case, based on properties of the ground where construction is planned, construction specifications, conditions of a jet stream at the time of inspection, or a distance (La) from the nozzle (N) to the pressure sensing unit (2). Moreover, it is possible to use an injection pressure being required for penetrating into the construction ground, e.g., 1 m, for determining the threshold values and prescribed values.

Advantageous Effects of the Invention

According to the present invention, since the jet nozzle (N) with the long ground penetrating (cutting) distance used in the large diameter jet grouting method is inspected by using the pressure sensing unit (2) and the controlling device (10), digital data corresponding to a pressure distribution, when the jet stream (J) impacts the pressure sensing unit (2), can be saved (registered) and the quality (of the nozzle N) can be determined.

Consequently, as different from an inspection of the prior art in which pressure sensitive paper is used in order to determine merely whether a fixed or higher pressure has been applied, a pressure distribution per unit time or per frame can be observed when the jet stream (J) impacts the pressure sensing unit (2), and it is possible to observe a fluctuation in pressure within an arbitrary numerical value range in the pressure distribution.

Additionally, according to the present invention, it is possible to obtain an area and the center coordinates of a range at which the jet stream (J) impacts the pressure sensing unit (2).

Here, in a case that an average value of pressures, which are enable to penetrate (pressures which enable to penetrate into the construction ground for a necessary distance) merely in the pressure distribution sensed by the pressure sensing unit (2) per frame, is equal to or more than a numeral value with which penetration into the construction ground is enabled for the necessary distance, it is possible to penetrate into construction ground by the jet stream (J) ejected from the nozzle (N).

According to the present invention, "calculating an average value of pressures which enable to penetrate (pressures which enable to penetrate or cut into construction ground for a necessary distance) merely in a pressure distribution sensed by the pressure sensing unit (2) in each of frame, and for determining whether a first ratio is equal to or more than a first prescribed value (e.g., 70%), said first ratio is a ratio of frames, in each of which a pressure being equal to or more than a first threshold value (a numerical value with which penetration into the construction ground is enabled for a necessary distance) is sensed, to a total number of frames where pressures from the nozzle (N) as the inspection target have been detected" is one of reference conditions for determining the quality (of a nozzle). Thus, the nozzle (N) which can penetrate positively into the soil is determined so as to fulfill one of the reference conditions for determining the quality (of a nozzle).

Further, in a case that an area of a region where the pressures being enable to penetrate (the pressures which enable to penetrate into the construction ground for a necessary distance) are distributed is small but larger than zero, it means that the jet stream impacts the sensing unit (2) in a state where the jet stream excellently converges without diffusing.

According to the present invention, "calculating an area of a region where the pressures being enable to penetrate are distributed, and for determining whether a second ratio is equal to or more than a second prescribed value (e.g., 90%), said second ratio is a ratio of frames, an area of each of which is greater than zero but is not greater than a second threshold value, to the total number of frames where the pressures from the nozzle (N) as the inspection target have been detected" is likewise one of the reference conditions for determining the quality. Therefore, the nozzle (N) which can eject the jet stream (J) excellently converged without diffusing is determined so as to fulfill one of the reference conditions for determining the quality.

Furthermore, in a case that the jet stream (J) can keep to impact the sensing unit (2) to a prescribed range during the inspection, it means that the jet stream (J) converges and can keep conditions so as to penetrate into the prescribed range.

According to the present invention, "determining coordinates of pressure center in each frame, and for determining whether a third ratio is equal to or more than a third prescribed value (e.g., 90%), said third ratio is a ratio of frames, in each of which the pressure center coordinates is located within a prescribed range (e.g., within a circular region having a center which is an average value of the pressure center coordinates and having a diameter which is triple a nozzle diameter), to the total number of frames where the pressures from the nozzle (N) as the inspection target have been detected" is likewise one of the reference conditions for determining the quality.

Thus, the nozzle (N) which can eject the jet stream (J) to keep impacting in the prescribed range for a fixed time can be determined to meet one of the reference conditions for determining the quality. In other words, according to the present invention, a nozzle (N), which makes a position that the jet stream (J) ejected therefrom impacts is non-uniform and unstable, is not determined to be a good product.

DESCRIPTION OF EMBODIMENTS

An embodiment according to the present invention will now be described hereinafter with reference to the accompanying drawings.

Figure 1:
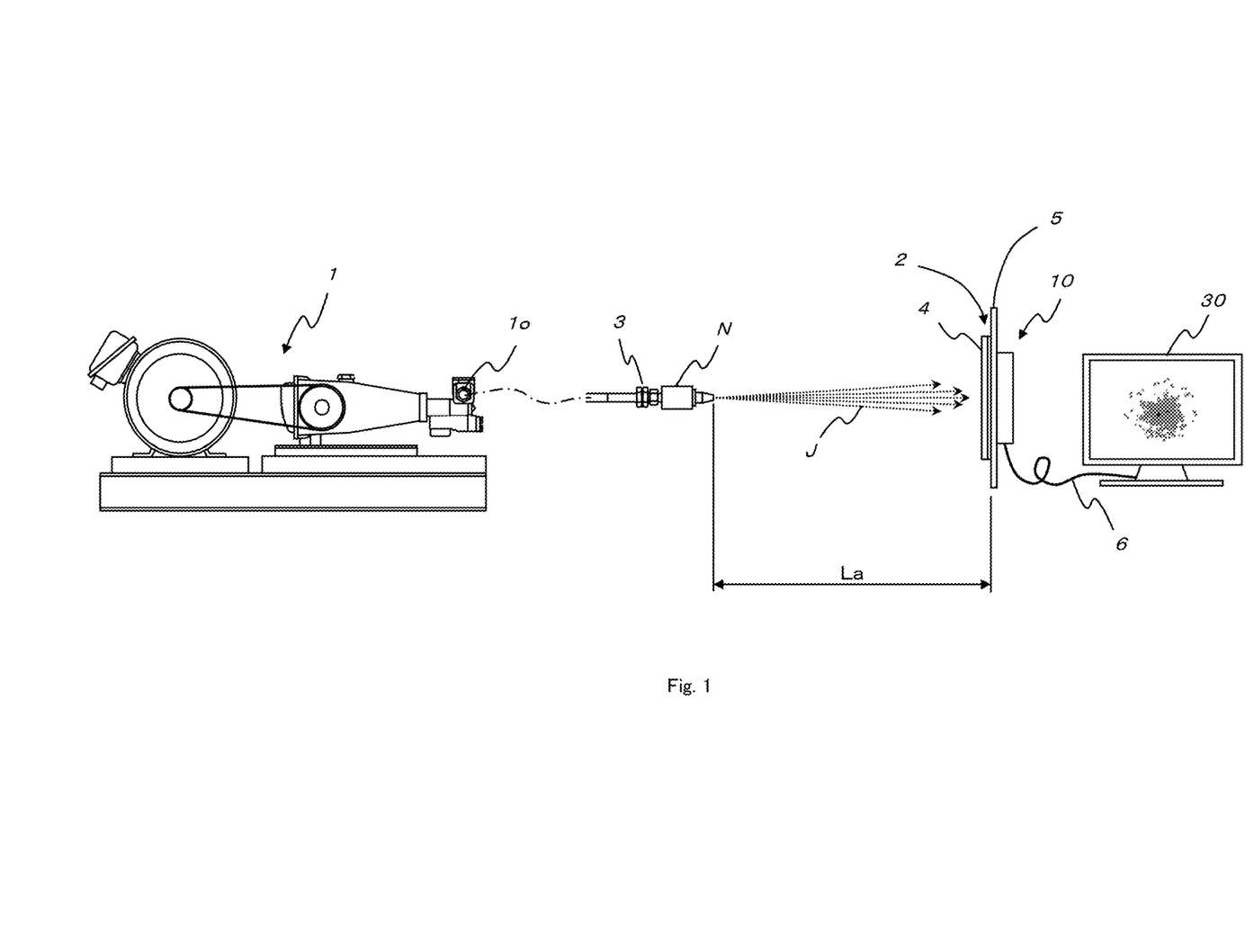
FIG. 1 is a block diagram showing an embodiment according to the present invention.

In FIG. 1, a determining device according to the embodiment of the present invention includes a jet stream generating device (a generating pump) 1, a pressure sensing unit (a pressure sensor) 2, a controlling device (a control unit) 10, and a monitor 30 as a display device.

A nozzle N as an inspection target is disposed to an attachment 3, and the attachment 3 is fixedly provided at one end (a right end in FIG. 1) of a non-illustrated pipeline. Additionally, the other end of the non-illustrated pipeline communicates with an outlet port 10 of the generating pump 1.

A front surface (a left surface in FIG. 1) of the pressure sensor 2 is covered with a protective sheet 4 as a protective member so that it is protected from impact of a high-pressure jet stream ejected from the nozzle N.

A back surface (a right surface in FIG. 1) of the pressure sensor 2 is fixed to a sensor fixing plate 5. In the sensor fixing plate 5, the control unit 10 is arranged on a surface on an opposite side (a back side in FIG. 1) of the pressure sensor 2, and the control unit 10 is connected with the monitor 30 through a communication cable 6.

In FIG. 1 (at the time of inspection: at the time of determination), a distance La from a tip of the nozzle N to the surface of the fixing plate 5 on which the pressure sensor 2 is fixed is determined in correspondence with an improvement range (a radius of an underground consolidation body) in a construction region or on the basis of similar rules.

In the monitor 30, a desired measurement result, e.g., a pressure distribution at each moment detected (measured) by the pressure sensor 2 or a state of pressure distributions which are superimposed during an arbitrary time is displayed in a desired manner. Further, the control unit 10 is constructed to process and store data measured by the pressure sensor 2 as digital data.

Reference sign J in FIG. 1 denotes a jet stream (a jet) ejected from the nozzle N.

FIG. 2 shows a measurement result per unit time, which is a frame showing merely numerals of portions to which pressures enabling penetration into construction ground for a necessary distance acted. In regard to this frame, for example, as shown in FIG. 3, a plurality of continuous frames can be shown in a superimposed manner.

Figure 3:
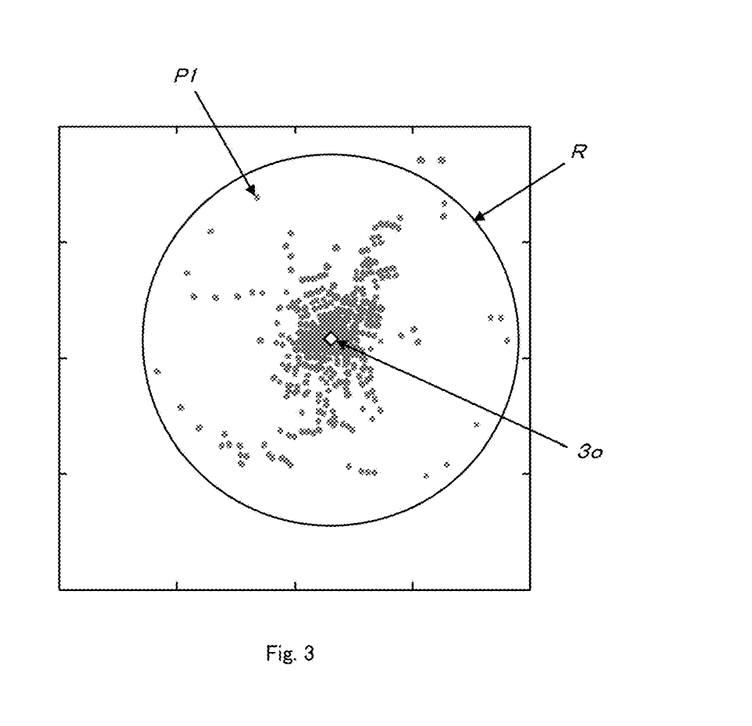
FIG. 3 is an explanatory drawing showing a predetermined number of frames in a superimposed manner.

A circle of a broken line in FIG. 2 indicates one point P1 (a plot: a pressure center coordinate) in FIG. 3. Here, in FIG. 3, for example, 1000 points (plots) are shown. Furthermore, in FIG. 2, an area FA in which numeral values are shown represents a region where pressures enabling penetration (pressures which enables penetration into the construction ground for a necessary distance) are detected.

In the illustrated embodiment, numeral data concerning pressures is raw data (raw) of an actual device (a measuring instrument) (for example, a device manufactured by Tekscan Company).

A circle represented by reference sign R in FIG. 3 has a center which represents an average value of, e.g., 1000 plots (pressure center coordinates), and it is a circle whose diameter is triple a diameter of the nozzle as the inspection target. Moreover, a ratio of frames having coordinates of pressure centers being present in the circle R to a total number of detected frames must be equal to or more than a prescribed value (a third prescribed value, e.g., 90%) as one necessary condition to determine a "non-defective product" (a step S7 and the like in FIG. 5).

The control unit 10 will now be described with reference to FIG. 4.

Figure 4:
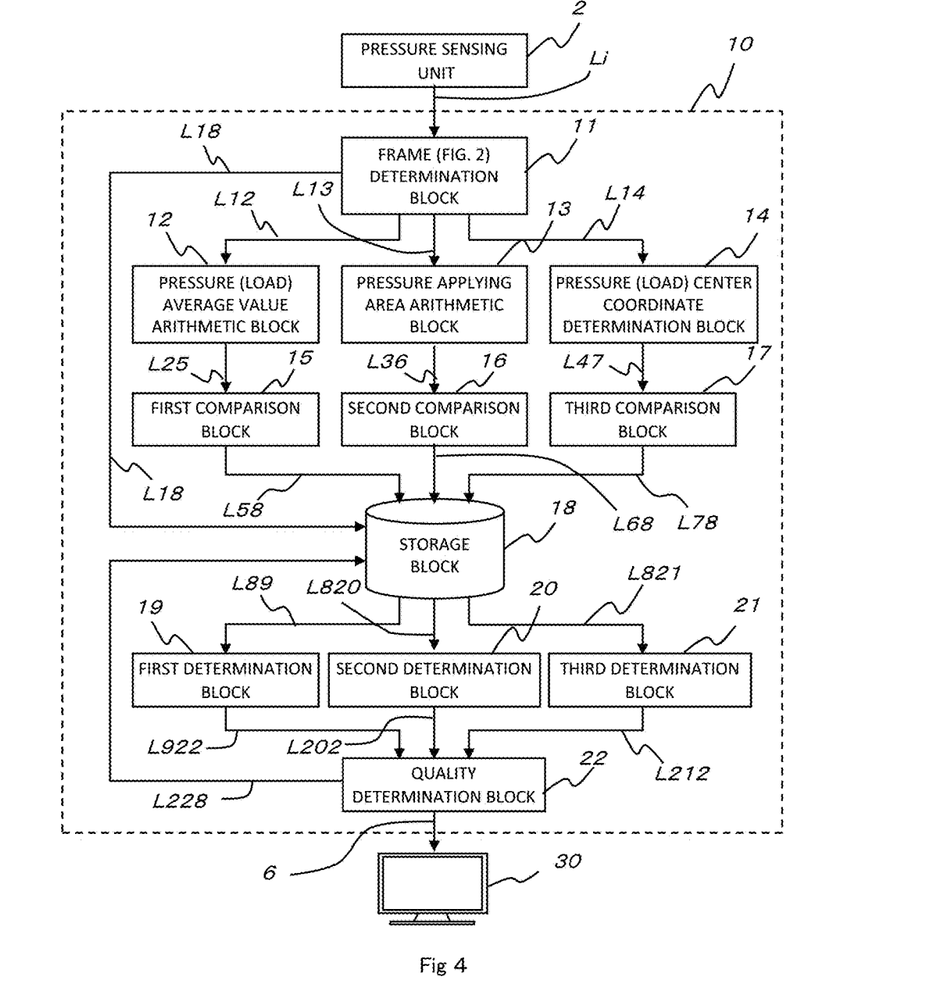
FIG. 4 is a functional block diagram showing a controlling device used in the embodiment.

In FIG. 4, the control unit 10 includes a frame determination block 11, a pressure average value arithmetic block 12, a pressure acting area arithmetic block 13, a pressure center coordinate determination block 14, a first comparison block 15, a second comparison block 16, a third comparison block 17, a storage block 18, a first determination block 19, a second determination block 20, a third determination block 21, and a quality determination block 22.

The frame determination block 11 is connected with the pressure sensor 2 through a line Li, connected to the pressure average value arithmetic block 12, the pressure acting area arithmetic block 13, and the pressure center coordinate arithmetic block 14 through a line L12, a line L13, and a line L14 respectively, and connected to the storage block 18 through a line L18.

Additionally, the frame determination block 11 has a function to determine a frame in a unit time (see FIG. 2) on the basis of information from the pressure sensor 2. Further, it has a function to superimpose a plurality of frames. Furthermore, the frame determination block 11 has a function to convert a determined frame into digital data (a digital signal) and transmit the data to the storage block 18.

The storage block 18 stores the above-mentioned data.

The pressure average value arithmetic block 12 has a function to select pressures which enable penetration (pressures which enable penetration into the construction ground for a necessary distance) in a pressure distribution in accordance with each frame determined by the frame determination block 11, calculate an average value of the selected pressures (the pressures enabling penetration) alone, and transmit a result (data of a pressure average value) to the first comparison block 15. Moreover, the pressure average value arithmetic block 12 is connected with the first comparison block 15 through a line L25.

The pressure acting area arithmetic block 13 has a function to calculate an area (a pressure acting area) where the pressures enabling penetration (the pressures which enable penetration into the construction ground for a necessary distance) are acting in accordance with each frame determined by the frame determination block 11 and transmit a result (data of the pressure acting area) to the second comparison block 16, and it is connected to the second comparison block 16 through a line L36.

The pressure center coordinate determination block 14 has a function to determine pressure center coordinates in accordance with each frame determined by the frame determination block 11 and transmits a result (data of the pressure center coordinates) to the third comparison block 17, and it is connected to the third comparison block 17 through a line L47.

The first comparison block 15 has a function to compare the pressure average value, i.e., the average value of the pressures enabling penetration (the pressures which enable penetration into the construction ground for a necessary distance) alone in the pressure distribution calculated in accordance with each frame by the pressure average value arithmetic block 12 with a first threshold value (a numeral value with which penetration into the construction ground is enabled for a necessary distance) stored in a non-illustrated storage section provided in the first comparison block 15, and perform comparison to determine whether the pressure average value is equal to or more than the first threshold value. Moreover, it also has a function to transmit the comparison result to the storage block 18, and is connected to the storage block 18 through a line L58.

It is to be noted that, although not shown, the first threshold value may be stored in the storage block 18 without providing the storage section in the first comparison block 15 so that the first threshold value stored in the storage block 18 is compared with the pressure average value calculated by the pressure average value arithmetic block 12 in the first comparison block 15. In this case, the line L58 serves as a bi-directional communication line.

The second comparison block 16 has a function to determine whether the pressure acting area (an area where the pressures enabling penetration are acting: an area where the pressures enabling penetration into the construction ground for a necessary distance) calculated in accordance with each frame by the pressure acting area arithmetic block 13 is greater than zero. In addition, the pressure acting area arithmetic block 13 has a function to compare the pressure acting area with a second threshold value stored in the non-illustrated storage section provided in the second comparison block 16 and determine whether the pressure acting area is not greater than the second threshold value by the comparison if said pressure acting area is greater than zero. Further, it also has a function to transmit the comparison result to the storage block 18, and is connected with the storage block 18 through a line L68.

It is to be noted that, although not shown, the second threshold value may be stored in the storage block 18 without providing the storage section in the second comparison block 16 so that the second threshold value stored in the storage block 18 is compared with the pressure acting area calculated by the pressure acting area arithmetic block 13 in the second comparison block 16. In this case, the line L68 serves as a bi-directional communication line.

The third comparison block 17 has a function to determine whether the pressure center coordinates determined by the pressure center coordinate determination block 14 in accordance with each frame are present within a prescribed range (within the circle R in FIG. 3: for example, within a circular region whose center corresponds to an average value of 1000 plots (pressure center coordinates) and whose diameter is triple the nozzle diameter) of a coordinate system stored in the non-illustrated storage section provided in the third comparison block 17. Furthermore, it has a function to transmit the comparison result to the storage block 18, and is connected to the storage block 18 through a line L78.

It is to be noted that, although not shown, the prescribed range (within the circle R in FIG. 3: for example, within the circular region whose center corresponds to an average value of 1000 plots (pressure center coordinates) and whose diameter is triple the nozzle diameter) of the coordinate system may be stored in the storage block 18 without providing the storage section in the third comparison block 17 so that whether the pressure center coordinates determined in accordance with each frame by the pressure center coordinate determination block 14 are present in said prescribed range stored in the storage block 18 is determined by the comparison in the third comparison block 17. In this case, the line L78 serves as a bi-directional communication line.

The first determination block 19 has a function to determine whether a ratio (a first ratio) of frames, each of which has said average value of pressures (the average value of pressures enabling penetration into the construction ground for a necessary distance alone) stored in the storage block 18 being not smaller than the first threshold value (the numerical value with which penetration into the construction ground is enabled for a necessary distance), to a total number of frames where pressures from the nozzle N as the inspection target have been detected is equal to or more than a first prescribed value (e.g., 70%). Furthermore, the first determination block 19 is connected to the storage block 18 through a line L89, and connected to the quality determination block 22 through a line L922.

The determination result of the first determination block 19 is immediately transmitted to the quality determination block 22.

The second determination block 20 has a function to determine whether a ratio (a second ratio) of frames, each of which has a value of said pressure area (an area where pressures enabling penetration are acting: an area where pressures enabling penetration in the constructed ground for a necessary distance are acting) stored in the block 18 being not greater than the second threshold value, to the total number of frames in which pressures from the nozzle N as the inspection target have been detected is equal to or more than a second prescribed value (e.g., 90%). Further, the second determination block 20 is connected to the storage block 18 through a line L820, and connected to the quality determination block 22 through a line L202.

The determination result of the second determination block 20 is immediately transmitted to the quality determination block 22.

The third determination block 21 has a function to determine whether a ratio (a third ratio) of frames, each of which has coordinates of pressure centers in each frame stored in the storage block 18 being present within a prescribed range (the circle R in FIG. 3: for example, a circular region whose center corresponds to an average value of 1000 plots (pressure center coordinates) and whose diameter is triple the nozzle diameter), to the total number of frames in which pressures from the nozzle N as the inspection target have been detected is equal to or more than a third prescribed value (e.g., 90%). Furthermore, the third determination block 21 is connected to the storage block 18 through a line L821, and connected to the quality determination block 22 through a line L212.

The determination result of the third determination block 21 is immediately transmitted to the quality determination block 22.

The quality determination block 22 has a function to determine the nozzle N as the inspection target to be a non-defective product only when the determination made by the first determination block is "the first ratio is equal to or more than the first prescribed value", the determination made by the second determination block is "the second ratio is equal to or more than the second prescribed value", and the determination made by the third determination block is "the third ratio is equal to or more than the third prescribed value", and determine the nozzle N as the inspection target to be a defective product in any other case. Moreover, the quality determination block 22 is connected to the storage block 18 through a line L228, and also connected to the monitor 30 other than the control unit 10 through the line communication cable 6.

It is to be noted that determinations in the above-mentioned various functions and processes to make these determinations can be displayed in the monitor 30 in a freely selectable manner.

A procedure and control in the nozzle quality determination according to the illustrated embodiment will now be described mainly with reference to FIG. 5.

Figure 5:
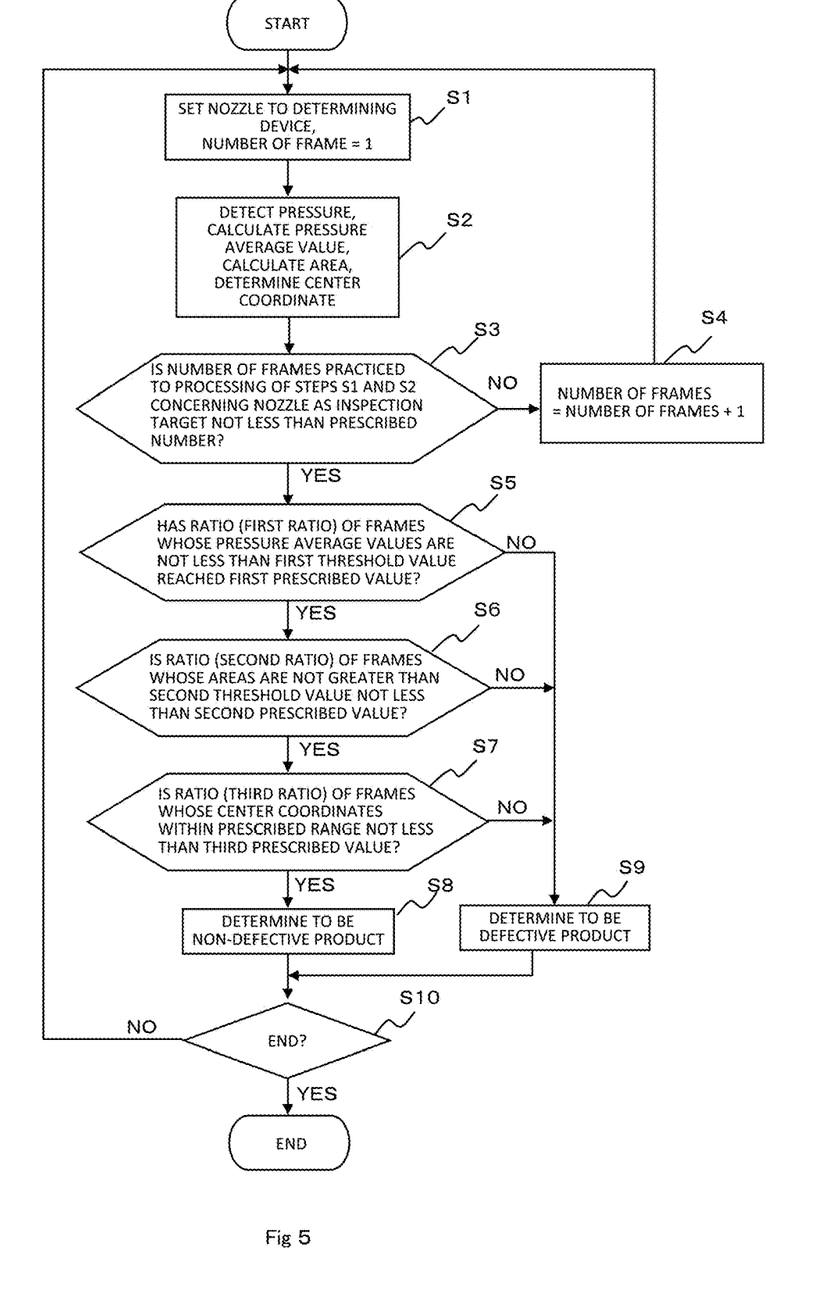
FIG. 5 is a flowchart showing control executed in the embodiment.

At a step S1 in FIG. 5, the nozzle N as the inspection target is disposed to the attachment 3 of the determining device shown in FIG. 1.

At a next step S2, pressures are detected in a unit time, a pressure average value (an average value of pressures which enable penetration in a pressure distribution only: an average value of pressures which enable penetration into the construction ground for a necessary distance merely) is calculated, a pressure acting area (an area where pressures enabling penetration are acting: an area where pressures enabling penetration into the construction ground for a necessary distance are acting) is obtained, and a center coordinates (the center of the circle R in FIG. 3: for example, an average value of 1000 plots or pressure center coordinates) of this area is determined.

At a step S3 following the step S2, whether the number of frames practiced to the processing of the steps S1 to S2 concerning the nozzle as the inspection target has reached a predetermined number is determined.

If a number of frames has reached the predetermined number ("YES" at the step S3), processing of steps advances to a step S5.

If the number of frames has not reached the predetermined number ("NO" at the step S3), the number of frames is increased at a step S4 (the next frame is determined), and the step S1 to the step S3 are repeated.

Here, in the illustrated embodiment, for example, if a nozzle diameter d=4.2 mm;

a distance L from the nozzle to the pressure sensing unit=1680 mm (400 times larger than the nozzle diameter d); and an ejected flow rate Q=120 litters/min, then the first threshold value=55 (a dimensionless quantity indicative of a dynamic pressure) (an actual machine/a measuring instrument: raw data (raw) of a device manufactured by Tekscan Company;

the second threshold value=50 ($mm^2$);

the prescribed range: a range within a circle having a diameter 3$d$;

the first prescribed value=70%;

the second prescribed value=90%; and the third prescribed value=90%.

At the step S5, the control unit 10 determines whether a ratio (the first ratio) of the frames each having said pressure average value which is equal to or more than the first threshold value to the total number of frames is equal to or more than the first prescribed value (70%).

If the ratio (the first ratio) of the frames each having said pressure average value which is equal to or more than the first threshold value to the total number of frames is equal to or more than the first prescribed value (70%) ("YES" at the step S5), the processing advances to a step S6.

On the other hand, if the ratio (the first ratio) of the frames each having said pressure average value which is equal to or more than the first threshold value to the total number of frames is less than the first prescribed value (70%) ("NO" at the step S5), the processing advances to a step S9. At the step S9, the quality determination block 22 of the control unit 10 determines that the inspection target nozzle is a "defective product", and the processing advances to a step S10.

At the step S6, the control unit 10 determines whether the ratio (the second ratio) of the frames each having said pressure acting area which is not greater than the second threshold value to the total number of frames is equal to or more than the second prescribed value (90%).

If the ratio (the second ratio) of the frames each having said pressure acting area which is not greater than the second threshold value to the total number of frames is equal to or more than the second prescribed value (90%) ("YES" at the step S6), the processing advances to a step S7.

On the other hand, if the ratio (the second ratio) of frames each having said pressure acting area which is not greater than the second threshold value to the total number of frames is less than the second prescribed value (90%) ("NO" at the step S6), the processing advances to a step S9. At the step S9, the quality determining block 22 of the control unit 10 determines that the inspection target nozzle is a "defective product", and the processing advances to a step S10.

At the step S7, the control unit 10 determines whether the ratio (the third ratio) of the frames each having the coordinates of pressure centers within the prescribed range (in the illustrated example, the circle R in FIG. 3: for example, a circular region whose center corresponds to an average value of 1000 plots (pressure center coordinates) and whose diameter is triple the nozzle diameter) to the total number of frames is equal to or more than the third prescribed value (90%).

If the ratio (the third ratio) of the frames each having the coordinates of pressure centers within said prescribed range to the total number of frames is equal to or more than the third prescribed value (90%) ("YES" at the step S7), the processing advances to a step 8.

On the other hand, if the ratio (the third ratio) of the frames each having the coordinates of pressure centers within said prescribed range to the total number of frames is less than the third prescribed value (90%) ("NO" at the step S7), the processing advances to the step S9. At the step S9, the quality determination block 22 of the control unit 10 determines that the inspection target nozzle is a "defective product", and the processing advances to the step S10.

If the step S8, i.e., the steps S5, S6, and S7 all have a result "YES", the quality determination block 22 of the control unit 10 determines that the inspection target nozzle is a "non-defective product". Moreover, the processing advances to the step S10.

At the step S10, the control unit 10 determines whether the quality determination of the nozzle is to be terminated.

If the quality determination of the nozzle is to be terminated ("YES" at the step S10), the determining device is stopped. If the quality determination of the nozzle is to continue ("NO" at the step S10), the processing returns to the step S1, and the step S1 and subsequent steps are repeated.

According to the determining device and the determining method of the illustrated embodiment, since the jet nozzle N for a jet stream with a long ground penetrating distance used in the large diameter jet grouting method is inspected by using the pressure sensor 2 and the control unit 10, digital data concerning a pressure distribution can be saved when the jet stream J impacts the pressure sensor 2, thereby the quality can be determined.

Consequently, as different from inspection using conventional pressure sensitive paper to determine only whether a fixed or higher pressure has acted, the pressure distribution when the jet stream J impacts the pressure sensor 2 can be observed, and a fluctuation in an arbitrary pressure range in the pressure distribution can be observed.

Furthermore, according to the illustrated embodiment, an area of the range where the jet stream J impacts the pressure sensing unit 2 and its center coordinate can be determined.

Here, if the average value of the pressures enabling penetration (the pressures enabling penetration into the construction ground for a necessary distance) in the pressure distribution only is equal to or more than the numeral value with which penetration into the construction ground is enabled for a necessary distance, the jet stream J ejected from the nozzle N assuredly enables penetration into the soil.

According to the illustrated embodiment, determining "whether the ratio (the first ratio) of the frames, each of which has the average value of the pressures enabling penetration (the pressure enabling penetration into the construction ground for a necessary distance) in the pressure distribution only being equal to or more than the first threshold value (the numeral value with which penetration into the construction ground is enabled for a necessary distance), to the total number of frames where the pressures from the nozzle N as the inspection target have been detected is equal to or more than the first prescribed value (e.g., 70%)" is one of criteria to determine whether the nozzle N is a non-defective product which assuredly enables penetration into the soil.

Further, if the area where the pressures enabling penetration are acting (the area where the pressures enabling penetration into the construction ground for a necessary distance) is small, it means that the jet stream impacts the pressure sensor 2 in an excellently converged state without diffusing.

According to the illustrated embodiment, determining "whether the ratio (the second ratio) of the frames, each of which has the area where the pressures enabling penetration has acted (the area where the pressures enabling penetration into the ground for a necessary distance has acted) being greater than zero and not greater than the second threshold value, to the total number of frames where the pressures from the nozzle N as the inspection target have been detected is equal to or more than the second prescribed value (e.g., 90%)" is likewise one of the criteria to determine whether the nozzle N is a non-defective product which can perform injection (of the jet stream. J) in an excellently converged state without diffusing.

Furthermore, if the jet stream J keeps impacting within the prescribed range (the circle R in FIG. 3: for example, within a circular region whose center corresponds to an average value of 1000 plots or pressure center coordinates and whose diameter is triple the nozzle diameter) of the pressure sensor 2 during an inspection, it means that the jet stream J is uniform and can keep penetration within the prescribed range.

According to the illustrated embodiment, determining "whether the ratio (the third ratio) of the frames, each of which has the pressure center coordinates of the frame within the prescribed range (the circle R in FIG. 3: for example, within a circular region whose center corresponds to an average value of 1000 plots or the pressure center coordinates and whose diameter is triple the nozzle diameter), to the total number of frames where the pressures from the nozzle N as the inspection target have been detected is equal to or more than the third prescribed value (e.g., 90%) is likewise one of the criteria to determine whether the nozzle N is a non-defective product.

Thus, the nozzle N which enables the jet stream J ejected therefrom to continuously impact within the prescribe range over a fixed time is determined to meet one of the determination criteria as a non-defective product.

In other words, according to the illustrated embodiment, the nozzle N which makes positions the ejected jet stream J impacts non-uniform and unstable is not erroneously determined to be a "non-defective product".

It is added that the illustrated embodiment is just an illustrative example and not intended to restrict a technical scope of the present invention.

REFERENCE SIGNS LIST

1 . . . jet stream generating device/generating pump
2 . . . pressure sensing unit/pressure sensor
3 . . . attachment
4 . . . protective sheet
5 . . . sensor fixing plate
6 . . . communication cable
10 . . . controlling device/control unit
30 . . . monitor

The invention claimed is:

1. A determining device characterized in that the device comprises:
   a jet stream generating device having an outlet port to/from which a nozzle as an inspection target is attachable/detachable;
   a pressure sensing unit with which a jet stream ejected from the jet stream generating device collides; and
   a controlling device to which a measurement result signal from the pressure sensing unit is transmitted; and
   the controlling device having:
   a function for calculating an average value of pressures which enable to penetrate merely in a pressure distribution sensed by the pressure sensing unit in each frame, and for determining whether a first ratio is equal to or more than a first prescribed value, said first ratio is a ratio of frames, in each of which a pressure being equal to or more than a first threshold value is sensed, to a total number of frames where pressures from the nozzle as the inspection target have been detected;

a function for calculating an area of a region where the pressures being enable to penetrate are distributed, and for determining whether a second ratio is equal to or more than a second prescribed value, said second ratio is a ratio of frames, an area of each of which is greater than zero but is not greater than a second threshold value, to the total number of frames where the pressures from the nozzle as the inspection target have been detected;

a function for determining coordinate of pressure center in each frame, and for determining whether a third ratio is equal to or more than a third prescribed value, said third ratio is a ratio of frames, in each of which the pressure center coordinates is located within a prescribed range, to the total number of frames where the pressures from the nozzle as the inspection target have been detected; and a function for determining the nozzle as the inspection target to be a non-defective product in a case that the first ratio is equal to or more than the first prescribed value, the second ratio is equal to or more than the second prescribed value, and the third ratio is equal to or more than the third prescribed value, and for determining the nozzle as the inspection target to be a defective product in any other case.

2. A determining method, in which a nozzle as an inspection target is mounted onto an outlet port, a jet stream ejected from a jet stream generating device, and measurement results being measured by a pressure sensing unit when the jet stream impacts the pressure sensing unit are processed by a controlling device, characterized in that the method comprises:

a first determination step of for calculating an average value of pressures which enable to penetrate merely in a pressure distribution sensed by the pressure sensing unit in each of frame, and for determining whether a first ratio is equal to or more than a first prescribed value, said first ratio is a ratio of frames, in each of which a pressure being equal to or more than a first threshold value is sensed, to a total number of frames where pressures from the nozzle as the inspection target have been detected;

a second determination step for calculating an area of a region where the pressures being enable to penetrate are distributed, and for determining whether a second ratio is equal to or more than a second prescribed value, said second ratio is a ratio of frames, an area of each of which is greater than zero but is not greater than a second threshold value, to the total number of frames where the pressures from the nozzle as the inspection target have been detected;

a third determination step for determining coordinate of pressure center in each frame, and for determining whether a third ratio is equal to or more than a third prescribed value, said third ratio is a ratio of frames, in each of which the coordinate of the pressure center is located within a prescribed range, to the total number of frame where the pressures from the nozzle as the inspection target have been detected; and a step for determining the nozzle as the inspection target to be a non-defective product in a case that the first ratio is equal to or more than the first prescribed value, the second ratio is equal to or more than the second prescribed value, and the third ratio is equal to or more than the third prescribed value, and for determining the nozzle as the inspection target to be a defective product in any other case.

* * * * *